United States Patent
Gamache et al.

(10) Patent No.: US 6,645,978 B1
(45) Date of Patent: Nov. 11, 2003

(54) LIPOXIN $A_4$ AND ITS ANALOGS FOR THE TREATMENT OF DRY EYE

(75) Inventors: Daniel A. Gamache, Arlington, TX (US); Gustav Graff, Cleburne, TX (US); Mark R. Hellberg, Arlington, TX (US); Peter G. Klimko, Fort Worth, TX (US); John M. Yanni, Burleson, TX (US)

(73) Assignee: Alcon, Inc., Hunenberg (CH)

( * ) Notice: Subject to any disclaimer, the term of this patent is extended or adjusted under 35 U.S.C. 154(b) by 0 days.

(21) Appl. No.: 09/787,789

(22) PCT Filed: Nov. 8, 2000

(86) PCT No.: PCT/US00/30707

§ 371 (c)(1),
(2), (4) Date: Mar. 23, 2001

(87) PCT Pub. No.: WO01/34144

PCT Pub. Date: May 17, 2001

Related U.S. Application Data

(60) Provisional application No. 60/164,406, filed on Nov. 9, 1999.

(51) Int. Cl.$^7$ ........................... A61K 9/00; A61K 81/20; A61K 47/24; A61P 27/02
(52) U.S. Cl. ....................... 514/310; 514/822; 514/925; 514/954; 514/947; 514/506; 514/512; 514/678; 514/715; 514/717; 514/724; 514/730; 424/407; 424/427; 424/428
(58) Field of Search .................................. 514/310, 822, 514/925, 954, 947, 506, 512, 678, 715, 717, 724, 730, 738, 739; 424/407, 427, 428

(56) References Cited

U.S. PATENT DOCUMENTS

| | | |
|---|---|---|
| 3,991,759 A | 11/1976 | Urquhart |
| 4,131,651 A | 12/1978 | Shah et al. |
| 4,370,325 A | 1/1983 | Packman |
| 4,409,205 A | 10/1983 | Shively |
| 4,576,758 A | 3/1986 | Morris |
| 4,744,980 A | 5/1988 | Holly |
| 4,753,945 A | 6/1988 | Gilbard et al. |
| 4,804,539 A | 2/1989 | Guo et al. |
| 4,818,537 A | 4/1989 | Guo |
| 4,868,154 A | 9/1989 | Gilbard et al. |
| 4,883,658 A | 11/1989 | Holly |
| 4,914,088 A | 4/1990 | Glonek et al. |
| 4,966,773 A | 10/1990 | Gressel et al. |
| 5,041,434 A | 8/1991 | Lubkin |
| 5,075,104 A | 12/1991 | Gressel et al. |
| 5,174,988 A | 12/1992 | Mautone et al. |
| 5,278,151 A | 1/1994 | Korb et al. |
| 5,290,572 A | 3/1994 | MacKeen |
| 5,294,607 A | 3/1994 | Glonek et al. |
| 5,371,108 A | 12/1994 | Korb et al. |
| 5,403,841 A | 4/1995 | Lang et al. |
| 5,441,951 A | 8/1995 | Serhan |
| 5,455,265 A | 10/1995 | Chandraratna |
| 5,578,586 A | 11/1996 | Glonek et al. |
| 5,620,921 A | 4/1997 | Sullivan |
| 5,696,166 A | 12/1997 | Yanni et al. |
| 5,800,807 A | 9/1998 | Hu et al. |

FOREIGN PATENT DOCUMENTS

| | | |
|---|---|---|
| EP | 0459148 A | 12/1991 |
| WO | 9013292 | 11/1990 |
| WO | 9429262 A | 12/1994 |
| WO | 9716179 A | 5/1997 |
| WO | 9811049 A | 3/1998 |

OTHER PUBLICATIONS

Kulkarni, "Steroidal and Non–steroidal Drugs in Endotoxin–Induced Uveitis," *Journal of Ocular Pharmacology*, 10(1):329–334 (1994).

Baudouin C, et al., "Flow cytometry in Impression Cytology Specimens: A new method for evaluation of conjunctival inflammation," *Invest Ophthalmol. Vis. Sci.*, 38(7):1458–1464 (1997).

Chiang et al., "Aspirin–Triggered 15–epi–Lipoxin $A_4$ (ATL) Generation by Human Leukocytes and Murine Peritonitis Exudates: Development of a Specific 15–epi–$LXA_4$ ELISA," *Pharmacol. Exp. Ther.*, 287(2):779–790 (1998).

Clish et al., "Local and Systemic Delivery of a Stable Aspirin–Triggered Lipoxin Prevents Neutrophil Recruitment in vivo," *Proc. Natl. Acad. Sci.*, 96(14):8247 (1999).

Dartt et al., "Vasoactive intestinal peptide–stimulated glycocongjugate secretion from conjunctival goblet cells," *Experimental Eye Research*, 63:27–34 (1996).

Dilly et al., "Surface Changes in the Anaesthetic Conjunctiva in Man, with Special Reference to the Production of Mucus from a Non–Goblet–Cell Source," *British Journal of Ophthalmology*, 65:833–842 (1981).

Gewirtz et al., "Pathogen–induced Chemokine Secretion from Model Intestinal Epithelium is Inhibited by Lipoxin $A_4$ Analogs," *J. Clin. Invest.*, 101(9):1860–1869 (1998).

Gewirtz et al., "$LXA_4$ Aspirin–Triggered 15–epi–$LXA_4$, and Their Analogs Selectively Downregulate PMN Azurophilic Degranulation," *Am. J. Physiol.*, 276(4, Part 1), C988–C994 (1999).

Greiner et al., "Mucus Secretory Vesicles in Conjunctival Epithelial Cells of Wearers of Contact Lenses," *Archives of Ophthalmology*, 98:1843–1846 (1980).

Lemp, "Report of the Nation Eye Institute/Industry Workshop on Clinical Trials in Dry Eyes," *The CLAO Journal*, 21(4):221–231 (1995).

(List continued on next page.)

*Primary Examiner*—Frederick Krass
*Assistant Examiner*—Clinton Ostrup
(74) *Attorney, Agent, or Firm*—Barry L. Copeland

(57) ABSTRACT

Ophthalmic compositions containing Lipoxin $A_4$ and its analogs and methods of their use for treating dry eve are disclosed.

5 Claims, No Drawings

OTHER PUBLICATIONS

Maddox et al., "Lipoxin $A_4$ Stable Analogs Are Potent Mimetics That Stimulate Human Monocytes and THP-1 Cells via a G-protein-linked Lipoxin $A_4$ Receptor," *J. Biol. Chem.*, 272(11):6972–6978 (1997).

Marom et al., "Human Airway Monohydroxyeicosatetraenoic Acid Generation and Mucous Release," *Journal of Clinical Investigation*, 72:122–127 (1983).

Marsh P and Pflugfelder SC, "Topical nonpreserved methylprednisolone therapy for keratoconjunctivitis sicca in Sjögren's syndrome," *Ophthalmology*, 106(1):811–816 (1999).

McCulley and Shine, "Tear film structure and dry eye," *Contactologia*, 20(4):145–49 (1998).

Nakamura et al., "Gefarnate stimulates secretion of mucin-like glycoproteins by corneal epithelium in vitro and protects corneal epithelium from desiccation in vivo," *Experimental Eye Research*, 65:569–574 (1997).

Pflugfelder SC, et al., "Altered cytokine balance in the tear fluid and conjunctiva of patients with Sjögren's syndrome keratoconjunctivitis sicca," *Curr. Eye Res.* 19(3):201–211 (1999).

Scalia et al., "Lipoxin $A_4$ Stable Analogs Inhibit Leukocyte Rolling and Adherence in the Rat Mesenteric Microvasculature: Role of P-Selectin," *Proc. Natl. Acad. Sci.*, 94(18):9967–9972 (1997).

Serhan, C.N. et al., "Lipoxin A Stereochemistry and Biosynthesis," *J. Biol. Chem.*, 261(35):16340–16345 (1986).

Serhan, C.N., "On the Relationship Between Leukotriene and Lipoxin Production by Human Neutrophils: Evidence for Differential Metabolism," *Bioch. Biophys. Acta*, 1004(2):158–168 (1989).

Serhan et al., "Design of Lipoxin $A_4$ Stable Analogs That Block Transmigration and Adhesion of Human Neutrophils," *Biochemistry*, 34(44):14609–14615 (1995).

Serhan N. et al., "Lipoxin and Aspirin-Triggered 15-epi-Lipoxin Cellular Interactions Anti-Inflammatory Lipid Mediators," *Clin. Chem. Lab. Med.*, 37:299–309 (1999).

Shine and McCulley, "Keratoconjunctivitis Sicca Associated with Meibomian Secretion Polar Lipid Abnormality," *Archives of Ophthalmology*, 116(7):849–52 (1998).

Stern ME, et al., "A Unified Theory of the Role of the Ocular Surface in Dry Eye," In: Sullivan et al., eds. Lacrimal Gland, Tear Film, and Dry Eye Syndromes 2, New York, Plenum, 1998, pp. 643–651.

Takano et al., "Neutrophil-mediated Changes in Vascular Permeability are Inhibited by Topical Application of Aspirin-triggered 15-epi-lipoxin $A_4$ and Novel Lipoxin $B_4$," *J. Clin. Invest.*, 101(4):819–826 (1998).

Watanabe et al., "Human Corneal and Conjuctival Epithelia Produce a Mucin-Like Glycoprotein for the Apical Surface," *Investigative Ophthalmology and Visual Science (IOVS)*, 36(2):337–344 (1995).

Yanni et al., "Effect of Intravenously Administered Lipoxygenase Metabolites on Rat Trachael Mucous Gel Layer Thickness," *International Archives of Allergy And Applied Immunology*, 90:307–309 (1989).

LIPOXIN A$_4$ AND ITS ANALOGS FOR THE TREATMENT OF DRY EYE

This application claims the benefit of provisional application Ser. No. 60/164,406 filed Nov. 9, 1999.

The present invention is directed to Lipoxin A$_4$ and related compounds in ophthalmic compositions and methods of their use. The compounds are particularly useful in treating dry eye.

BACKGROUND OF THE INVENTION

Dry eye, also known generically as keratoconjunctivitis sicca, is a common ophthalmological disorder affecting millions of Americans each year. The condition is particularly widespread among post-menopausal women due to hormonal changes following the cessation of fertility. Dry eye may afflict an individual with varying severity. In mild cases, a patient may experience burning, a feeling of dryness, and persistent irritation such as is often caused by small bodies lodging between the eye lid and the eye surface. In severe cases, vision may be substantially impaired. Other diseases, such as Sjogren's disease and cicatricialpemphigoid may also manifest dry eye complications.

Dry eye consists of a variety of conditions of diverse origin which affect the tear film and the ocular surface. Dry eye is a disorder of the precorneal tear film due to tear deficiency or excessive tear evaporation which causes damage to the interpalpebral ocular surface and is associated with symptoms of ocular discomfort. Symptoms which include burning, stinging and photophobia are associated with clinical signs of interpalpebral surface damage and tear instability hyperosmolarity. Dry eye is a consequence of a variety of pathogenic causes and afflicts individuals with a broad range of severity. However, a common denominator in dry eye patients is the breakdown of the ocular tear film resulting in dehydration and damage to the exposed ocular surface.

Dry eye occurs in patients with Sjogren's syndrome, an autoimmune disease which destroys the lacrimal gland and reduces tear production. Approximately 75% of people over the age of 65 suffer from dry eye as tear production decreases with the normal aging process. Hormonal changes occurring during pregnancy, lactation, oral contraceptive use, menstruation and menopause can cause dry eye. Dry eye can occur when ocular surface changes occur in rheumatoid arthritis, diabetes, thyroid abnormalities, asthma, cataracts, glaucoma and lupus. Medications which induce dry eye by decreasing tear production include antidepressants, decongestants, antihistamines, antihypertensives, oral contraceptives, diuretics and anti-ulcer agents. Dry eye can result from exposure to smoke, fluorescent lights, air pollution, wind, heaters, air conditioning. Lack of blinking during computer use can elicit signs and symptoms of dry eye. The condition can result from living in a dry climate or exposure to dry conditions such as in airline travel. Dry eye can result from unusual facial anatomy which affects blinking, or irregularities of the cornea which result in uneven tear distribution. Decreased tear lipid production occurs in infection or inflammation of the meibomian glands, resulting in excessive tear evaporation. Decreased corneal sensitivity can also lead to insufficient reflex tearing and decreased blinking. This can occur as a result of trauma to the eye, for example nerve damage due to flap formation in LASIK surgical procedures or from the corneal photoablation effected by such procedures, or in severe keratitis or excessive contact lens wear.

Although it appears that dry eye may result from a number of unrelated pathogenic causes, all presentations of the complication share a common effect, that is the breakdown of the pre-ocular tear film, which results in dehydration of the exposed outer surface of the eye and many of the symptoms outlined above (Lemp, Report of the National Eye Institute/Industry Workshop on Clinical Trials in Dry Eyes, *The CLAO Journal*, volume 21, number 4, pages 221–231 (1995)).

Practitioners have taken several approaches to the treatment of dry eye. One common approach has been to supplement and stabilize the ocular tear film using so-called artificial tears instilled throughout the day. Other approaches include the use of ocular inserts that provide a tear substitute or stimulation of endogenous tear production.

Examples of the tear substitution approach include the use of buffered, isotonic saline solutions, aqueous solutions containing water soluble polymers that render the solutions more viscous and thus less easily shed by the eye. Tear reconstitution is also attempted by providing one or more components of the tear film such as phospholipids and oils. Phospholipid compositions have been shown to be useful in treating dry eye; see, e.g., McCulley and Shine, Tear film structure and dry eye, *Contactologia*, volume 20(4), pages 145–49 (1998); and Shine and McCulley, Keratoconjunctivitis sicca associated with meibomian secretion polar lipid abnormality, *Archives of Ophthalmology*, volume 116(7), pages 849–52 (1998). Examples of phospholipid compositions for the treatment of dry eye are disclosed in U.S. Pat. No. 4,131,651 (Shah et al.), U.S. Pat. No. 4,370,325 (Packman), U.S. Pat. No. 4,409,205 (Shively), U.S. Pat. Nos. 4,744,980 and 4,883,658 (Holly), U.S. Pat. No. 4,914,088 (Glonek), U.S. Pat. No. 5,075,104 (Gressel et al.), U.S. Pat. No. 5,278,151 (Korb et al.), U.S. Pat. No. 5,294,607 (Glonek et al.), U.S. Pat. No. 5,371,108 (Korb et al.), and U.S. Pat. No. 5,578,586 (Glonek et al.). U.S. Pat. No. 5,174,988 (Mautone et al.) discloses phospholipid drug delivery systems involving phospholipids, propellants and an active substance.

U.S. Pat. No. 3,991,759 (Urquhart) discloses the use of ocular inserts in the treatment of dry eye. Other semi-solid therapy has included the administration of carrageenans (U.S. Pat. No. 5,403,841, (Lang)) which gel upon contact with naturally occurring tear film.

Another approach involves the provision of lubricating substances in lieu of artificial tears. For example, U.S. Pat. No. 4,818,537 (Guo) discloses the use of a lubricating, liposome-based composition, and U.S. Pat. No. 5,800,807 (Hu et al.) discloses compositions containing glycerin and propylene glycol for treating dry eye.

Aside from the above efforts, which are directed primarily to the alleviation of symptoms associated with dry eye, methods and compositions directed to treatment of the underlying dry eye condition have also been pursued. For example, U.S. Pat. No. 5,041,434 (Lubkin) discloses the use of sex steroids, such as conjugated estrogens, to treat dry eye condition in post-menopausal women; U.S. Pat. No. 5,290,572 (MacKeen) discloses the use of finely divided calcium ion compositions to stimulate pre-ocular tear film production; and U.S. Pat. No. 4,966,773 (Gressel et al.) discloses the use of microfine particles of one or more retinoids for ocular tissue normalization.

Although these approaches have met with some success, problems in the treatment of dry eye nevertheless remain. The use of tear substitutes, while temporarily effective, generally requires repeated application over the course of a patient's waking hours. It is not uncommon for a patient to have to apply artificial tear solution ten to twenty times over the course of the day. Such an undertaking is not only disruptive and time consuming, but is also potentially very expensive.

The use of ocular inserts is also problematic. Aside from cost, they are often unwieldy and uncomfortable. Further, as foreign bodies introduced in the eye, they can be a source of contamination leading to infections. In situations where the insert does not itself produce and deliver a tear film, artificial tears must still be instilled on a regular and frequent basis.

Mucins are proteins which are heavily glycosylated with glucosamine-based moieties. Mucins provide protective and lubricating effects to epithelial cells, especially those of mucosal membranes. Mucins have been shown to be secreted by vesicles and discharged on the surface of the conjunctival epithelium of human eyes (Greiner et al., Mucus Secretory Vesicles in Conjunctival Epithelial Cells of Wearers of Contact Lenses, *Archives of Ophthalmology*, volume 98, pages 1843–1846 (1980); and Dilly et al., Surface Changes in the Anaesthetic Conjunctiva in Man, with Special Reference to the Production of Mucus from a Non-Goblet-Cell Source, *British Journal of Ophthalmology*, volume 65, pages 833–842 (1981)). A number of human-derived mucins which reside in the apical and subapical corneal epithelium have been discovered and cloned (Watanabe et al., Human Corneal and Conjunctival Epithelia Produce a Mucin-Like Glycoprotein for the Apical Surface, *Investigative Ophthalmology and Visual Science*, volume 36, number 2, pages 337–344 (1995)). Recently, Watanabe discovered a new mucin which is secreted via the cornea apical and subapical cells as well as the conjunctival epithelium of the human eye (Watanabe et al., *IOVS*, volume 36, number 2, pages 337–344 (1995)). These mucins provide lubrication, and additionally attract and hold moisture and sebaceous material for lubrication and the corneal refraction of light.

Mucins are also produced and secreted in other parts of the body including lung airway passages, and more specifically from goblet cells interspersed among tracheal/bronchial epithelial cells. Certain arachidonic acid metabolites have been shown to stimulate mucin production in these cells. Yanni reported the increased secretion of mucosal glycoproteins in rat lung by hydroxyeicosatetraenoic acid ("HETE") derivatives (Yanni et al., Effect of Intravenously Administered Lipoxygenase Metabolites on Rat Trachael Mucous Gel Layer Thickness, *International Archives of Allergy And Applied Immunology*, volume 90, pages 307–309 (1989)). Similarly,Marom has reported the production of mucosal glycoproteins in human lung by HETE derivatives (Marom et al., Human Airway Monohydroxy-eicosatetraenoic Acid Generation and Mucous Release, *Journal of Clinical Investigation*, volume 72, pages 122–127 (1983)).

Agents claimed for increasing ocular mucin and/or tear production include vasoactive intestinal polypeptide (Dartt et. al., Vasoactive intestinal peptide-stimulated glycocongfugate secretion from conjunctival goblet cells, *Experimental Eye Research*, volume 63, pages 27–34, (1996)), gefarnate (Nakmura et al., Gefarnate stimulates secretion of mucin-like glycoproteins by corneal epithelium in vitro and protects corneal epithelium from dessication in vivo, Experimental Eye Research, volume 65, pages 569–574 (1997)), liposomes (U.S. Pat. No. 4,818,537), androgens (U.S. Pat. No. 5,620,921), melanocycte stimulating hormones (U.S. Pat. No. 4,868,154), phosphodiesterase inhibitors (U.S. Pat. No. 4,753,945), and retinoids (U.S. Pat. No. 5 5,455,265).

However, many of these compounds or treatments suffer from a lack of specificity, efficacy and potency and none of these agents have been marketed so far as therapeutically useful products to treat dry eye and related ocular surface diseases.

U.S. Pat. No. 5,696,166 (Yanni et al.) discloses compositions containing naturally occurring HETEs, or derivatives thereof, and methods of use for treating dry eye. Yanni et al. discovered that compositions comprising HETEs increase ocular mucin secretion when administered to a patient and are thus useful in treating dry eye.

It is known that under certain conditions 15-HETE can be converted by activated leukocytes to Lipoxin $A_4$ (Serhan, C.N., *Bioch. Biophys. Acta*, volume 1004, page 158 (1989); Serhan, C. N., et al.,*J. Biol. Chem.*, volume 261, page 16340 (1986)). It has also been discovered that aspirin treatment of activated leukocytes induces the biosynthesis of 15-epi-Lipoxin $A_4$ from arachidonic acid via the intermediacy of 15R-HETE (Serhan, N. et al., *J. Pharmacol. Exp. Ther.*, volume 287, page 779 (1998), and Serhan, N. et al., *Clin. Chem. Lab. Med.*, volume 37, page 299, (1999)), and that inflammatory processes may contribute to ocular surface abnormalities in dry eye conditions. Stem ME, et al., A unified theory of the role of the ocular surface in dry eye, In: Sullivan et al., eds. Lacrimal Gland, Tear Film, and Dry Eye Syndromes 2, New York, Plenum, 1998, pp. 643–651. Expression of proinflammatory cytokines in tears (Pflugfelder SC, et al., Altered cytokine balance in the tear fluid and conjunctiva of patients with Sjogren 's syndrome keratoconjunctivitis sicca, *Curr. Eye Res.* 19(3):201–211 (1999)), and of markers of inflammation on the ocular surface of patients with Sj6gren's and non-Sjogren's keratoconjunctivitis sicca has been reported (Baudouin C, et al., Flow cytometry in Impression Cytology Specimens: A new method for evaluation of conjunctival inflammation. Invest Ophthalmol. Vis. Sci. 38:1458–1464 (1997)), and anti-inflammatory steroids have demonstrated therapeutic efficacy in dry eye patients (Marsh P and Pflugfelder SC, Topical nonpreserved methylprednisolone therapy for keratoconjunctivitis sicca in Sjogren's syndrome, *Ophthalmology*, 106:811–816 (1999)). Nothing in the foregoing references, however, discloses or suggests an anti-inflammatory contribution by Lipoxin $A_4$ to the preservation of corneal integrity in the dry eye model.

In view of the foregoing, there is a need for an effective, convenient treatment for dry eye that is capable of alleviating symptoms, as well as treating the underlying physical and physiological deficiencies of dry eye.

SUMMARY OF THE INVENTION

The present invention is directed to compositions and methods of use. The compounds are particularly useful in the treatment of dry eye-type diseases and disorders requiring the wetting of the eye. More specifically, the present invention discloses the use of Lipoxin $A_4$ and its analogs, the preferred compositions of which are typically administered topically to the eye for the treatment of dry eye.

DETAILED DESCRIPTION OF THE INVENTION

The present invention is directed to compositions containing Lipoxin A4 and its analogs and their methods of use. It is believed that, among other utilities, the compounds of the present invention stimulate ocular mucin production and/or secretion following topical ocular application and are therefore believed to be useful in treating dry eye. These compounds are of formula I:

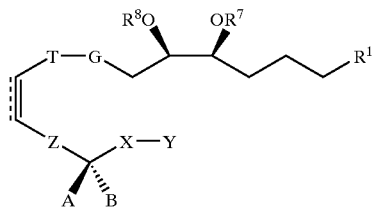

wherein:
$R^1$ is $CO_2R$, $CONR^2R^3$, $CH_2OR^4$, $CH_2NR^5R^6$, $CH_2N_3$, $CH_2$-Hal, $CH_2NO_2$, $CH_2SR^{20}$, $COSR^{21}$, or 2,3,4,5-tetrazol-1-yl, wherein:
R is H, or $CO_2R$ forms a pharmaceutically acceptable salt or a pharmaceutically acceptable ester;
$NR^2R^3$ and $NR^5R^6$ are the same or different and comprise a free or functionally modified amino group, e.g., $R^2$, $R^3$, $R^5$ and $R^6$ are the same or different and are H, alkyl, cycloalkyl, aralkyl, aryl, OH, or alkoxy, with the proviso that at most only one of $R^2$ and $R^3$ are OH or alkoxy and at most only one of $R^5$ and $R^6$ are OH or alkoxy;
$OR^4$ comprises a free or functionally modified hydroxy group, e.g., $R^4$ is H, acyl;
alkyl, cycloalkyl, aralkyl, or aryl;
Hal is F, Cl, Br or I;
$R^{20}$ a free or functionally modified thiol group; and
$R^{21}$ is H, or $COSR^{21}$ forms a pharmaceutically acceptable salt or a pharmaceutically acceptable thioester;
$OR^7$ and $OR^8$ are the same or different and comprise a free or functionally modified hydroxy group;
G, T, and Z are the same or different and are $CH_2CH_2$, cis- or trans-$CH=CH$, or $C\equiv C$;||| is $C\equiv C$ or cis-$CH=CH$;
one of A, B is H or $CH_3$, and the other is a free or functionally modified hydroxy group, or A-B comprises a double bonded oxygen, or A-B is $OCH_2CH_2O$;
X is $CR^{11}R^{12}(CH_2)_q$ or $CR^{11}R^{12}(CH_2)_qO$, where q is 0–6; and $R^{11}$ and $R^{12}$ are the same or different and are H or $CH_3$;
Y is $CH_3$, or a phenyl ring optionally substituted with alkyl, halo, trihalomethyl, acyl, or a free or functionally modified hydroxy, thiol, or amino group;
or X-Y is $(CH_2)_pY^1$, where p is 0–6, and

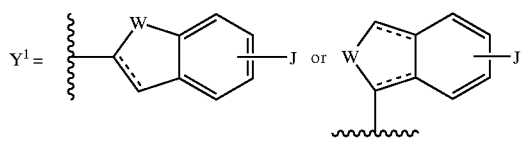

wherein:
W is $CH_2$, O, $S(O)_m$, $NR^{10}$, $CH_2CH_2$, $CH=CH$, $CH_2O$, $CH_2S(O)_m$, $CH=N$, or $CH_2NR^{10}$; where m is 0–2; and $NR^{10}$ is NH or a functionally modified amino group;
J is H, alkyl, acyl, halo, trihalomethyl, or a free or functionalized hydroxy, thiol, or amino group; and $=$ is a single or double bond;
or X-Y is a substituted or unsubstituted cyclohexyl.

The compounds of formula (I) may also be incorporated into phospholipids as glyceryl esters or sphingomyelin amides. Phospholipid sphingomyelin amides of the compounds of formula (I) will typically comprise a formula (I) compound amidated via its carbon 1 carboxylate to the amino group of the sphingomyelin backbone. The phospholipid formula (I) esters will comprise various phospholipids. Phospholipid esters of the compounds of formula (I) will typically comprise a formula (I) compound esterified via its carbon 1 carboxylate to the sn-1 or sn-2 position alcohol, or both, of the glycerol backbone of the phospholipid. If the sn-1 or sn-2 position of the glyceryl ester class does not contain an ester of a compound of formula (I), then such carbon positions of the glycerol backbone will comprise a methylene, ether or ester moiety linked to a substituted or unsubstituted $C_{12-30}$ alkyl or alkenyl (the alkenyl group containing one or more double bonds); alkyl(cycloalkyl) alkyl; alkyl(cycloalkyl); alkyl(heteroaryl); alkyl(heteroaryl) alkyl; or alkyl-M-Q; wherein the substitutent is alkyl, halo, hydroxy, or functionally modified hydroxy; M is O or S; and Q is H, alkyl, alkyl(cycloalkyl)alkyl, alkyl(cycloalkyl), alkyl (heteroaryl) or alkyl(heteroaryl)alkyl. However, at least one of the sn-1 or sn-2 position alcohols of the glycerol backbone must form an ester with a compound of formula (I) via the carbon 1 carboxylate of the latter. Preferred phospholipid-formula (I) esters will be of the phosphatidylethanolamine, phosphatidylcholine, phosphatidylserine, and phospatidylinositol type. The most preferred phospholipid-formula (I) esters will comprise a formula (I) compound esterified via its carbon 1 carboxylate to the alcohol at the sn-2 position of phosphatidylcholine, phosphatidylethanolamine or phosphatidylinositol. The phospholipid-formula (I) esters and sphingomyelin amides may be synthesized using various phospholipid synthetic methods known in the art; see for example, Tsai et al., *Biochemistry*, volume 27, page 4619 (1988); and Dennis et al., *Biochemistry*, volume 32, page 10185 (1993).

Included within the scope of the present invention are the individual enantiomers of the compounds of the present invention, as well as their racemic and non-racemic mixtures. The individual enantiomers can be enantioselectively synthesized from the appropriate enantiomerically pure or enriched starting material by means such as those described below. Alternatively, they may be enantioselectively synthesized from racemic/non-racemic or achiral starting materials. (Asymmetric Synthesis; J. D. Morrison and J. W. Scott, Eds.; Academic Press Publishers: New York, 1983–1985, volumes 1–5; Principles ofAsymmetric Synthesis; R. E. Gawley and J. Aube, Eds.; Elsevier Publishers: Amsterdam, 1996). They may also be isolated from racemic and non-racemic mixtures by a number of known methods, e.g. by purification of a sample by chiral HPLC (A Practical Guide to Chiral Separations by HPLC; G. Subramanian, Ed.; VCH Publishers: New York, 1994; Chiral Separations by HPLC; A.M. Krstulovic, Ed.; Ellis Horwood Ltd. Publishers, 1989), or by enantioselective hydrolysis of a carboxylic acid ester sample by an enzyme (Ohno, M.; Otsuka, M. *Organic Reactions*, volume 37, page 1 (1989)). Those skilled in the art will appreciate that racemic and non-racemic mixtures may be obtained by several means, including without limitation, nonenantioselective synthesis, partial resolution, or even mixing samples having different enantiomeric ratios. Departures may be made from such details within the scope of the accompanying claims without departing from the principles of the invention and without sacrificing its advantages. Also included within the scope of the present invention are the individual isomers substantially free of their respective enantiomers.

As used herein, the terms "pharmaceutically acceptable salt", "pharmaceutically acceptable ester", and "pharmaceutically acceptable thioester" mean any salt, ester, or thioester, respectively, that would be suitable for therapeutic administration to a patient by any conventional means without significant deleterious health consequences; and "ophthalmically acceptable salt", "ophthalmically acceptable ester", and "ophthalmically acceptable thioester" means any pharmaceutically acceptable salt, ester, or thioester, respectively, that would be suitable for ophthalmic application, i.e. non-toxic and non-irritating.

The term "free hydroxy group" means an OH. The term "functionally modified hydroxy group" means an OH which has been functionalized to form: an ether, in which an alkyl, aryl, cycloalkyl, heterocycloalkyl, alkenyl, cycloalkenyl, heterocycloalkenyl, alkynyl, or heteroaryl group is substituted for the hydrogen; an ester, in which an acyl group is substituted for the hydrogen; a carbamate, in which an aminocarbonyl group is substituted for the hydrogen; or a carbonate, in which an aryloxy-, heteroaryloxy-, alkoxy-, cycloalkoxy-, heterocycloalkoxy-, alkenyloxy-, cycloalkenyloxy-, heterocycloalkenyloxy-, or alkynyloxycarbonyl group is substituted for the hydrogen. Preferred moieties include OH, $OCH_2C(O)CH_3$, $OCH_2C(O)C_2H_5$, $OCH_3$, $OCH_2CH_3$, $OC(O)CH_3$, and $OC(O)C_2H_5$.

The term "free amino group" means an NH2. The term "functionally modified amino group" means an NH2 which has been functionalized to form: an aryloxy-, heteroaryloxy-, alkoxy-, cycloalkoxy-, heterocycloalkoxy-, alkenyl-, cycloalkenyl-, heterocycloalkenyl-, alkynyl-, or hydroxy-amino group, wherein the appropriate group is substituted for one of the hydrogens; an aryl-, heteroaryl-, alkyl-, cycloalkyl-, heterocycloalkyl-, alkenyl-, cycloalkenyl-, heterocycloalkenyl-, or alkynyl-amino group, wherein the appropriate group is substituted for one or both of the hydrogens; an amide, in which an acyl group is substituted for one of the hydrogens; a carbamate, in which an aryloxy-, heteroaryloxy-, alkoxy-, cycloalkoxy-, heterocycloalkoxy-, alkenyl-, cycloalkenyl-heterocycloalkenyl-, or alkynyl-carbonyl group is substituted for one of the hydrogens; or a urea, in which an aminocarbonyl group is substituted for one of the hydrogens. Combinations of these substitution patterns, for example an $NH_2$ in which one of the hydrogens is replaced by an alkyl group and the other hydrogen is replaced by an alkoxycarbonyl group, also fall under the definition of a functionally modified amino group and are included within the scope of the present invention. Preferred moieties include $NH_2$, $NHCH_3$, $NHC_2H_5$, $N(CH_3)_2$, $NHC(O)CH_3$, NHOH, and $NH(OCH_3)$.

The term "free thiol group" means an SH. The term "functionally modified thiol group" means an SH which has been functionalized to form: a thioether, where an alkyl, aryl, cycloalkyl, heterocycloalkyl, alkenyl, cycloalkenyl, heterocycloalkenyl, alkynyl, or heteroaryl group is substituted for the hydrogen; or a thioester, in which an acyl group is substituted for the hydrogen. Preferred moieties include SH, $SC(O)CH_3$, $SCH_3$, $SC_2H_5$, $SCH_2C(O)C_2H_5$, and $SCH_2C(O)CH_3$.

The term "acyl" represents a group that is linked by a carbon atom that has a double bond to an oxygen atom and a single bond to another carbon atom.

The termr "alkyl" includes straight or branched chain aliphatic hydrocarbon groups that are saturated and have 1 to 15 carbon atoms. The alkyl groups may be interrupted by one or more heteroatoms, such as oxygen, nitrogen, or sulfur, and may be substituted with other groups, such as halogen, hydroxyl, aryl, cycloalkyl, aryloxy, or alkoxy. Preferred straight or branched alkyl groups include methyl, ethyl, propyl, isopropyl, butyl and t-butyl.

The term "cycloalkyl" includes straight or branched chain, saturated or unsaturated aliphatic hydrocarbon groups which connect to form one or more rings, which can be fused or isolated. The rings may be substituted with other groups, such as halogen, hydroxyl, aryl, aryloxy, alkoxy, or lower alkyl. Preferred cycloalkyl groups include cyclopropyl, cyclobutyl, cyclopentyl and cyclohexyl.

The term "heterocycloalkyl" refers to cycloalkyl rings that contain at least one heteroatom such as O, S, or N in the ring, and can be fused or isolated. The rings may be substituted with other groups, such as halogen, hydroxyl, aryl, aryloxy, alkoxy, or lower alkyl. Preferred heterocycloalkyl groups include pyrrolidinyl, tetrahydrofuranyl, piperazinyl, and tetrahydropyranyl.

The term "alkenyl" includes straight or branched chain hydrocarbon groups having 1 to 15 carbon atoms with at least one carbon-carbon double bond, the chain being optionally interrupted by one or more heteroatoms. The chain hydrogens may be substituted with other groups, such as halogen. Preferred straight or branched alkenyl groups include, allyl, 1-butenyl, 1-methyl-2-propenyl and 4-pentenyl.

The term "cycloalkenyl" includes straight or branched chain, saturated or unsaturated aliphatic hydrocarbon groups which connect to form one or more non-aromatic rings containing a carbon-carbon double bond, which can be fused or isolated. The rings may be substituted with other groups, such as halogen, hydroxyl, alkoxy, or lower alkyl. Preferred cycloalkenyl groups include cyclopentenyl and cyclohexenyl.

The term "heterocycloalkenyl" refers to cycloalkenyl rings which contain one or more heteroatoms such as O, N, or S in the ring, and can be fused or isolated. The rings may be substituted with other groups, such as halogen, hydroxyl, aryl, aryloxy, alkoxy, or lower alkyl. Preferred heterocycloalkenyl groups include pyrrolidinyl, dihydropyranyl, and dihydrofuranyl.

The term "carbonyl group" represents a carbon atom double bonded to an oxygen atom, wherein the carbon atom has two free valences.

The term "aminocarbonyl" represents a free or flnctionally modified amino group bonded from its nitrogen atom to the carbon atom of a carbonyl group, the carbonyl group itself being bonded to another atom through its carbon atom.

The term "lower alkyl" represents alkyl groups containing one to six carbons ($C_1$–$C_6$).

The term "halogen" represents fluoro, chloro, bromo, or iodo.

The term "aryl" refers to carbon-based rings which are aromatic. The rings may be isolated, such as phenyl, or fused, such as naphthyl. The ring hydrogens may be substituted with other groups, such as lower alkyl, halogen, free or functionalized hydroxy, trihalomethyl, etc. Preferred aryl groups include phenyl, 3-(trifluoromethyl)phenyl, 3-chlorophenyl, and 4-fluorophenyl.

The term "heteroaryl" refers to aromatic hydrocarbon rings which contain at least one heteroatom such as O, S, or N in the ring. Heteroaryl rings may be isolated, with 5 to 6 ring atoms, or fused, with 8 to 10 atoms. The heteroaryl ring(s) hydrogens or heteroatoms with open valency may be substituted with other groups, such as lower alkyl or halogen. Examples of heteroaryl groups include imidazole, pyridine, indole, quinoline, furan, thiophene, pyrrole, tetrahydroquinoline, dihydrobenzofuran, and dihydrobenzindole.

The terms "aryloxy", "heteroaryloxy", "alkoxy", "cycloalkoxy", "heterocycloalkoxy", "alkenyloxy", "cycloalkenyloxy", "heterocycloalkenyloxy", and "alkynyloxy" represent an aryl, heteroaryl, alkyl, cycloalkyl, heterocycloalkyl, alkenyl, cycloalkenyl, heterocycloalkenyl, or alkynyl group, respectively, attached through an oxygen linkage.

The terms "alkoxycarbonyl", "aryloxycarbonyl", "heteroaryloxycarbonyl", "cycloalkoxycarbonyl", "heterocycloalkoxycarbonyl", "alkenyloxycarbonyl", "cycloalkenyloxycarbonyl", "heterocycloalkenyloxycarbonyl", and "alkynyloxycarbonyl" represent an alkoxy, aryloxy, heteroaryloxy, cycloalkoxy, heterocycloalkoxy, alkenyloxy, cycloalkenyloxy, heterocycloalkenyloxy, or alkynyloxy group, respectively, bonded from its oxygen atom to the carbon of a carbonyl group, the carbonyl group itself being bonded to another atom through its carbon atom.

Preferred compounds of the present invention include those of formula I,
wherein:

$R^1$ is $CO_2R$, wherein R is H, or wherein $CO_2R$ forms an ophthalmically acceptable ester or salt;

$R^7$ and $R^8$ are H;

T, G, and Z are trans-CH=CH;∥
is cis-CH=CH;

one of A, B is OH, and the other is H or $CH_3$;

$X=CR^{11}R^{12}(CH_2)_q$ or $CR^{11}R^{12}(CH_2)_qO$, where q=0–6; and $R^{11}$ and $R^{12}$ are the same or different and are H or $CH_3$; and Y is $CH_3$, or a phenyl ring optionally substituted with alkyl, halo, or $CF_3$; or X-Y=cyclohexyl.

Among the particularly preferred compounds of formula I are the following compounds 1–6; compound 1 (Lipoxin $A_4$) is commercially available from Cayman Chemical Co. (Ann Arbor, Mich.) and from Sigma Chemical Co. (St. Louis, Mo.), while compounds 2–6 can be prepared as detailed in U.S. Pat. No. 5,441,951 and PCT International Application WO 9429262 Al, the entire contents of which are by this reference incorporated herein. Additional references disclosing other (non dry eye-related) biological activities of the individual compounds are as indicated in the table below.

| Compound Numbers | Reference |
|---|---|
| 3, 5 | Serhan, et al., Proc. Natl. Acad. Sci., 1999, 96 (14), 8247. |
| 1, 2, 3, 4, 5 | Serhan, et al., Am. J. Physiol., 1999, 276 (4, Part 1), C988. |
| 1, 2, 3, 4 | Serhan, et al., J. Clin. Invest., 1998, 101 (9), 1860. |
| 3, 4, 5 | Serhan, et al., J. Clin. Invest., 1998, 101 (4), 819. |
| 3, 4, 6 | Serhan, et al., Proc. Natl. Acad. Sci., 1997, 94 (18), 9967. |
| 1, 2, 3, 4 | Serhan, et. al., J. Biol. Chem., 1997, 272 (11), 6972. |
| 1, 2, 3, 4, 6 | Serhan, et al., Biochemistry, 1995, 34 (44), 14609. |

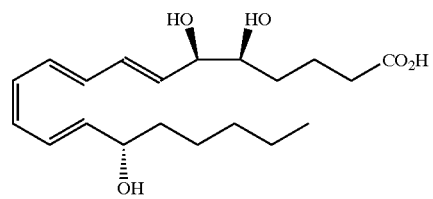

1

Salt forms of the formula (I) compounds are preferred as it is believed that the neat salts are more stable than the corresponding neat acids. Preferred salts of the present invention are those wherein a terminal carboxylate of formula (I) (i.e., wherein $R^1$ is $CO_2R$) forms a salt with cations selected from: $Na^+$, $K^+$, $NH_4^+$, benzyltrimethylammonium ion, tetrabutylammonium ion, and phenyltrimethyl ammonium ion.

As used hereinafter, the term "compounds of formula (I)," refers to compounds of formula (I), and/or the phospholipid-formula (I) esters or amides described above. The compositions of the present invention comprise one or more compounds of formula (I) and a pharmaceutically acceptable carrier. The compositions are formulated in accordance with methods known in the art for the particular route of administration desired for the prevention, treatment or amelioration of the particular disease or disorder targeted. As used herein, the term "pharmaceutically acceptable carrier" refers to any formulation which is safe, and provides the appropriate delivery of an effective amount of one or more compounds of formula (I) for the prevention, treatment or amelioration of the disease or disorder targeted.

As used herein, the term "pharmaceutically effective amount" refers to an amount of one or more compounds of formula (I) that, when administered to a patient, prevents, treats or ameliorates a disease or disorder, or conditions associated thereof. As used herein, "an ophthalmically effective amount" refers to an amount of one or more compounds of formula (I) that, when administered to a patient, prevents, treats or ameliorates an ophthalmic disease or disorder, or conditions associated thereof. For the treatment of glaucoma and/or ocular hypertension, such an effective amount will lower intraocular pressure ("IOP") and/or ameliorate conditions associated therewith. As used herein, "an effective amount to treat glaucoma and/or ocular hypertension" refers to an amount of one or more compounds of formula (I) that, when administered to a patient, lowers IOP and/or ameliorates the conditions associated thereof. For the treatment of dry eye, such an effective amount will stimulate secretion of mucin in the eye and thus eliminate or improve dry eye conditions when administered to the eye. As used herein, "an effective amount to treat dry eye" refers to an amount of one or more compounds of formula (I) that, when administered to a patient, prevents, treats or ameliorates a dry eye disease or disorder, or conditions associated therewith. Generally, the compounds of formula (I) will be contained in a composition of the present invention in a concentration range of about 0.00001 to 10 per cent weight/volume ("% w/v"). Preferred ophthalmic, including dry eye-treatment, compositions will contain one or more compounds of formula (I) in a concentration of from about 0.00001–0.01% w/v.

The present invention is particularly directed to compositions useful in treating dry eye. Preferably, such compositions will be formulated as solutions, suspensions and other dosage forms for topical administration. Aqueous solutions are generally preferred, based on ease of formulation, biological compatibility (especially in view of the malady to be treated, e.g., dry eye-type diseases and disorders), as well as a patient's ability to easily administer such compositions by means of instilling one to two drops of the solutions in the affected eyes. However, the compositions may also be suspensions, viscous or semi-viscous gels, or other types of solid or semi-solid compositions. Suspensions may be preferred for compounds of formula (I) which are less soluble in water.

Preferably, the ophthalmic compositions of the present invention will also contain ethanol. As used herein, "an effective concentration of ethanol" refers to a concentration that enhances the biological efficacy of the formula (I) compositions in vivo. In general, the concentration of ethanol necessary for the enhancement of the compounds of formula (I) is believed to be somewhat proportional to the concentration of the formula (I) compound(s) administered. If a relatively high concentration of formula (I) compound (s), e.g., above 0.01% w/v, is administered, the concentration of ethanol in such compositions may be proportionally less than analogous compositions containing lower concentrations of formula (I) compounds. In general, however, the ethanol concentration contained in the ophthalmic compositions of the present invention will range from about 0.001–2% w/v. Compositions containing formula (I) concentrations of about 0.00001–0.02% w/v preferably will contain ethanol in a concentration of about 0.005–0.2% w/v, and most preferably, about 0.02–0.10% w/v.

Preferably, the compositions of the present invention will also contain a surfactant. Various surfactants useful in topical ophthalmic formulations may be employed. The surfactant(s) may provide additional chemical stabilization of the formula (I) compounds and may further provide for the physical stability of the compounds. In other words, the surfactants may aid in preventing chemical degradation of the compounds of formula (I) and also prevent the compounds from binding to the containers in which their compositions are packaged. As used herein, "an effective concentration of surfactant(s)" refers to a concentration that enhances the chemical and physical stability of formula (I) compound(s). Examples of surfactants include, but are not limited to: Cremophor® EL, polyoxyl 20 ceto stearyl ether, polyoxyl 40 hydrogenated castor oil, polyoxyl 23 lauryl ether and poloxamer 407 may be used in the compositions. A preferred surfactant is polyoxyl 40 stearate. The concentration of surfactant will vary, depending on the concentration of formula (I) compound(s) and optional ethanol present in the formulation. In general, however, the surfactant(s) concentration will be about 0.001 to 2.0% w/v. Preferred compositions of the present invention will contain about 0.1% w/v of polyoxyl 40 stearate.

The compositions of the present invention may also include various other ingredients, such as tonicity agents, buffers, preservatives, co-solvents and viscosity building agents.

Various tonicity agents may be employed to adjust the tonicity of the composition, preferably to that of natural tears for ophthalmic compositions. For example, sodium chloride, potassium chloride, magnesium chloride, calcium chloride, dextrose and/or mannitol may be added to the composition to approximate physiological tonicity. Such an amount of tonicity agent will vary, depending on the particular agent to be added. In general, however, the compositions will have a tonicity agent concentration of about 0.1–1.5% w/v. Sodium chloride in the amount of 0.75% w/v is preferred.

An appropriate buffer system (e.g., sodium phosphate, sodium acetate, sodium citrate, sodium borate or boric acid) may be added to the compositions to prevent pH drift under storage conditions. The particular concentration will vary, depending on the agent employed. In general, however, such a concentration will range from about 0.02 to 2.0% w/v. Preferred compositions will contain about 0.25% w/v of boric acid.

Antioxidants may be added to compositions of the present invention to protect the formula (I) compounds from oxidation during storage. Examples of such antioxidants include, but are not limited to, vitamin E and analogs thereof, ascorbic acid and derivatives, and butylated hydroxyanisole (BHA).

Compositions formulated for the treatment of dry eye-type diseases and disorders may also comprise aqueous carriers designed to provide immediate, short-term relief of dry eye-type conditions. Such carriers can be formulated as a phospholipid carrier or an artificial tears carrier, or mixtures of both. As used in this paragraph and the immediately succeeding paragraph, the term "phospholipid" refers only to the phospholipids of the phospholipid carrier. It does not refer to a compound of formula (I) and, as such, does not contain a formula (I) compound. "Phospholipid carrier" and "artificial tears carrier" refer to aqueous compositions which: (i) comprise one or more phospholipids (in the case of phospholipid carriers) or other compounds, which lubricate, "wet," approximate the consistency of endogenous tears, aid in natural tear build-up, or otherwise provide temporary relief of dry eye symptoms and conditions upon ocular administration; (ii) are safe; and (iii) provide the appropriate delivery vehicle for the topical administration of an effective amount of one or more compounds of formula (I). Examples or artificial tears compositions useful as artificial tears carriers include, but are not limited to, commercial products, such as Tears Naturale®, Tears Naturale II®, Tears Naturale Free®, and Bion Tears® (Alcon Laboratories, Inc., Fort Worth, Tex.). Examples of phospholipid carrier formulations include those disclosed in U.S. Pat. No. 4,804,539 (Guo et al.), U.S. Pat. No. 4,883,658 (Holly), U.S. Pat. No. 4,914,088 (Glonek), U.S. Pat. No. 5,075,104 (Gressel et al.), U.S. Pat. No. 5,278,151 (Korb et al.), U.S. Pat. No. 5,294,607 (Glonek et al.), U.S. Pat. No. 5,371,108 (Korb et al.), U.S. Pat. No. 5,578,586 (Glonek et al.); the foregoing patents are incorporated herein by reference to the extent they disclose phospholipid compositions useful as phospholipid carriers of the present invention.

The phospholipids useful in the phospholipid carriers are any natural or synthetic phospholipid compound comprising a glycerol-phosphoric acid ester or sphingomyelin backbone. Examples of phospholipids useful in the present invention include those of formula (II):

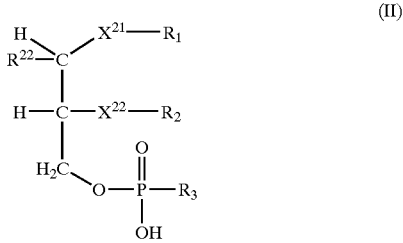

wherein, $X^{21}$ and $X^{22}$ are the same or different and are O, NH(C=O), O(C=O), or a direct bond;

$R^{22}$ is H or $CH=CH(CH_2)_{12}CH_3$;

$X^{21}$—$R^1$ is OH, or $R^1$ is $C_{12-26}$ substituted or unsubstituted alkyl or alkenyl;

$R^2$ is $C_{12-26}$ substituted or unsubstituted alkl or alkenyl; and $R^3$ is H, OH, $OCH_2CH(NH_3+)COO$, $OCH_2CH_2NH_3$, $OCH_2CH_2N(CH_3)_3$, $OCH_2CH(OH)CH_2OH$, and O-inositol.

The phospholipids may be present as racemic or nonracemic compounds. Preferred phospholipids are those wherein $X^{21}$—$R^1$ and/or $X^{22}$—$R^2$ comprise fatty acid esters or amides. Natural fatty acids are saturated, monounsaturated or polyunsaturated. Examples of fatty acid residues include, but are not limited to, laurate, myristate, palmitate, palmitoleate, stearate, oleate, linoleate, linolenate, eicosanoate, docosanoate and lignocerate. Preferred phospholipid types are the phosphatidylethanolamines, phosphatidylcholines, phosphatidylserines, phospatidylinositols and sphingomyelins. Examples of specific phospholipids include: 1,2-dipalmitoyl phosphatidyl choline ("DPPC") 1,2-dipalmityl phosphatidyl glycerol ("DPPG"), N-stearyl sphingomyelin, N-palmityl sphingomyelin, N-oleyl sphingomyelin, 1,2-distearoyl phosphatidyl ethanolamine ("DSPE"), 1,2-distearoyl phosphatidyl inositol ("DSPI"), 1-stearoyl-2-paimitoyl phosphatidyl ethanolamine ("SPPE"), I -stearoyl-2-palmitoyl phosphatidyl choline ("SPPC"), 1,2-dipalmitoyl phosphatidyl ethanolamine ("DPPE"), 1,2-dioleoyl phophatidyl ethanolamine ("DOPE"), 1,²dioleoyl phophatidyl serine ("DOPS"), and 1,2-dipalmitoyl phosphatidyl serine ("DPPS"). The most preferred phospholipid carriers are the phosphatidylethanolamines and sphingomyelins. Phospholipids are available from a variety of natural sources and may be synthesized by methods known in the art; see, for example, Tsai et al., biochemistry, volume 27, page 4619 (1988); and Dennis et. al., biochemistry, volume 32, page 10185 (1993).

Other compounds designed to lubricate, "set," approximate the consistency of endogenous tears, aid in natural tear build-up, or otherwise provide temporary relief of dry eye symptoms and conditions upon ocular administration the eye are known in the art. Such compounds may enhance the viscosity of the composition, and include, but are not limited to: monomeric polyols, such as, glycerol, propylene glycol, ethylene glycol; polymeric polyols, such as, polyethylene glycol, hydroxypropylmethyl cellulose ("HPMC"), carboxy methylcellulose sodium, hydroxy propylcellulose ("HPC"), dextrans, such as, dextran 70; water soluble proteins, such as gelatin; and vinyl polymers, such as, polyvinyl alcohol, polyvinly/pyrolidone povidone and carbomers, such as, carbomer 934P, carbomer 941, carbomer 940, carbomer 974P.

Other compounds may also be added to the ophthalmic compositions of the present invention to increase the viscosity of the carrier. Examples of viscosity enhancing agents include, but are not limited to: polysaccharides, such as hyaluronic acid and its salts, chondroitin sulfate and its salts, dextrans, various polymers of the cellulose family; vinyl polymers; and acrylic acid polymers. In general, the phospholipid carrier or artificial tears carrier compositions will exhibit a viscosity of 1 to 400 centipoises ("cps"). Preferred compositions containing artificial tears or phospholipid carriers will exhibit a viscosity of about 25 cps.

Topical ophthalmic products are typically packaged in multidose form. Preservatives are thus required to prevent microbial contamination during use. Suitable preservatives include: benzalkonium chloride, chlorobutanol, benzododecinium bromide, methyl paraben, propyl paraben, phenylethyl alcohol, edetate disodium, sorbic acid, polyquatemium-1, or other agents known to those skilled in the art. Such preservatives are typically employed at a level of from 0.001 to 1.0% w/v. Unit dose compositions of the present invention will be sterile, but typically unpreserved. Such compositions, therefore, generally will not contain preservatives.

The preferred compositions of the present invention are intended for administration to a human patient suffering from dry eye. Preferably, such compositions will be administered topically. In general, the doses used for the above described purposes will vary, but will be in an effective amount to increase mucin production in the eye and thus eliminate or improve dry eye conditions. Generally, 1–2 drops of such compositions will be administered 1–10 times per day for the treatment of dry eye or other ocular disease or disorder. Preferably, 1–2 drops of the compositions will be administered 1–4 times per day.

The present invention is also directed to stable, stock compositions comprising one or more compounds of formula (I) and ethanol. While bound by no theories, it may be that storing the compounds of formula (I) in an ethanolic solution provides greater stability of the compounds of formula (I) over analogous aqueous compositions, or neat compounds of formula (I) compositions. Such compositions comprise one or more compounds of formula (I) and an amount of ethanol to solubilize the compounds of formula (I) in solution. Preferably, the ethanolic stock solutions will contain anhydrous ethanol, but aqueous ethanolic solutions are also contemplated by the present invention. Generally, the stock solutions will contain ethanol in a concentration of about 25 to 100% volume/volume ("v/v"). Typically, such stock solutions will contain compounds of formula (I) in high concentration relative to the pharmaceutical compositions of the present invention.

The following Examples 1–5 describe preferred compositions of the present invention. The actual pH of the compositions may vary (e.g., between 6–8), and the concentrations of the various ingredients included in the exemplified compositions may vary, but are included in the compositions in the approximate amounts shown.

EXAMPLE 1

| Ingredient | Amount (% w/v) |
|---|---|
| Compound 1 | 0.00001–0.01 |
| Ethanol | 0.0505 |
| Polyoxyl 40 Stearate | 0.1 |
| Boric Acid | 0.25 |
| Sodium Chloride | 0.75 |
| Disodium Edetate | 0.01 |
| Polyquaternium-1 | 0.001 |
| NaOH/HCl | q.s., pH = 7.5 |
| Purified Water | q.s. 100% |

The above composition is prepared by the following method. The batch quantities of polyoxyl 40 stearate, boric acid, sodium chloride, disodium edetate, and polyquatenwum-1 are weighed and dissolved by stirring in 90% of the batch quantity of purified water. The pH is adjusted to 7.5±0.1 with NaOH and/or HCl. Under yellow light or reduced lighting, the batch quantity of Compound 1 as a stock solution in ethanol and the additional quantity of ethanol necessary for the batch are measured and added. Purified water is added to q.s. to 100%. The mixture is stirred for five minutes to homogenize and then filtered through a sterilizing filter membrane into a sterile recipient. Preferably, the above process is performed using glass, plastic or other non-metallic containers or containers lined with such materials.

EXAMPLE 2

| Ingredient | Amount (% w/v) |
|---|---|
| Compound 4 | 0.00001–0.01 |
| Ethanol | 0.005–0.2 |
| Polyoxyl 40 Stearate | 0.1 |
| Boric Acid | 0.25 |
| Sodium Chloride | 0.75 |
| Disodium Edetate | 0.01 |
| Polyquaternium-1 | 0.001 |
| NaOH/HCl | q.s., pH = 7.5 |
| Purified Water | q.s. 100% |

The above formulation may be made by a method similar to the method described in Example 1.

EXAMPLE 3

| Ingredient | Amount (% w/v) |
|---|---|
| Compound of formula (I) | 0.00001–0.01 |
| Polyoxyl 40 Stearate | 0.1 |
| Ethanol | 0.005–0.2 |
| Boric Acid | 0.25 |
| Sodium Chloride | 0.75 |
| NaOH/HCl | q.s., pH = 7.5 |
| Purified Water | q.s. 100% |

The above formulation may be made by a method similar to the method described in Example 1.

Example 4
The following is an example of an artificial tears carrier-composition of the present invention:

| Ingredient | Amount (% w/v) |
|---|---|
| Compound of formula (I) | 0.00001–0.01 |
| HPMC | 0.3 |
| Dextran 70 | 0.1 |
| Sodium Chloride | 0.8 |
| Potassium Chloride | 0.12 |
| Dibasic Sodium Phosphate | 0.025 |
| Disodium EDTA | 0.01 |
| Polyquaternium-1 | 0.001 + 10% excess |
| Purified Water | Qs |
| NaOH/HCl | qs to pH 6–8 |

The above formulation may be made by a method similar to the method described in Example 1.

EXAMPLE 5
The following is an example of a phospholipid carrier-composition of the present invention:

| Ingredient | Amount (% w/v) |
|---|---|
| Compound of formula (I) | 0.00001–0.01 |
| Ethanol | 0.005–0.2 |
| Polyoxyl 40 Stearate | 0.1 |
| DPPC | 0.05 |
| DPPE | 0.05 |
| Sodium Chloride | 0.8 |
| Potassium Chloride | 0.12 |
| Dibasic Sodium Phosphate | 0.025 |
| Disodium EDTA | 0.01 |
| Polyquaternium-1 | 0.001 + 10% excess |
| Purified Water | Qs |
| NaOH/HCl | qs to pH 6–8 |

The above formulation may be made by a method similar to the method described in Example 1.

The invention in its broader aspects is not limited to the specific details shown and described above. Departures may be made from such details within the scope of the accompanying claims without departing from the principles of the invention and without sacrificing its advantages.

What is claimed is:

1. A method for the treatment of dry eye, which comprises administering to a mammalian patient, a composition comprising a pharmaceutically acceptable carrier and a pharmaceutically effective amount of a compound is selected from the group consisting of:

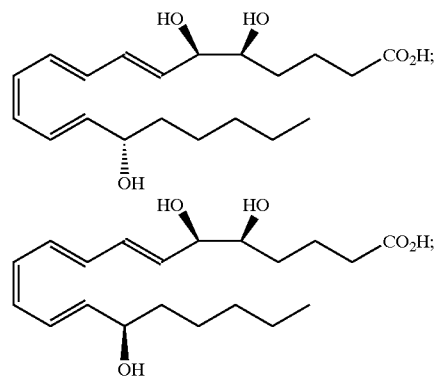

-continued

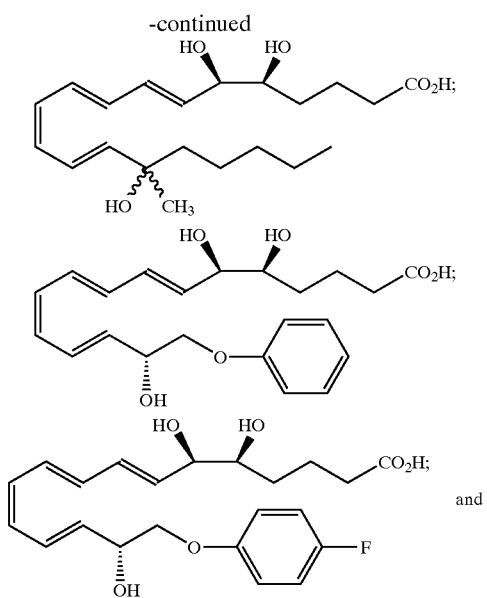

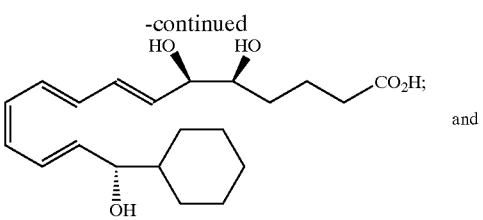

pharmaceutically acceptable salts and esters thereof.

2. The method of claim 1, wherein the composition is topically applied to an eye in need thereof.

3. The method of claim 2, wherein the dry eye is attendant to ocular trauma.

4. The method of claim 3, wherein the ocular trauma results from a surgical procedure or contact lens wear.

5. The method of claim 4, wherein the ocular trauma results from a surgical procedure and the surgical procedure includes keratotomy or corneal photoablation.

* * * * *